United States Patent [19]

Kuhn et al.

[11] Patent Number: 4,801,532

[45] Date of Patent: Jan. 31, 1989

[54] IMMUNOLOGICAL METHODS FOR DIAGNOSING NEUROCYSTICERCOSIS

[75] Inventors: Raymond E. Kuhn, Clemmons; John J. Estrada, Winston-Salem, both of N.C.; Max Grogl, Silver Spring, Md.

[73] Assignee: Wake Forest University, Winston-Salem, N.C.

[21] Appl. No.: 102,674

[22] Filed: Sep. 30, 1987

Related U.S. Application Data

[62] Division of Ser. No. 766,017, Aug. 15, 1985, Pat. No. 4,740,456.

[51] Int. Cl.⁴ .................. G01N 33/53; G01N 33/561; G01N 33/567
[52] U.S. Cl. .......................................... 435/7; 424/88; 436/516; 436/811; 530/395; 530/403; 530/413; 530/417; 530/855
[58] Field of Search .............. 435/7; 424/88; 436/516, 436/811; 530/395, 403, 413, 417, 855

[56] References Cited

U.S. PATENT DOCUMENTS 4,016,043  4/1977  Schuurs ................................ 435/7
4,298,685  11/1981  Parikh ................................. 435/7

OTHER PUBLICATIONS

Chemical Abstracts, 103:121318p (1985).
Mohammad, I. N. et al., J. Clin. Microbiol., 20(4), 775-779 (Oct. 1984).
Grogl, M. et al., J. Parasit., 71(4), 433-442 (1985).
Estrada, J. J. et al., Journal of the Neurological Sciences, 71, 39-48 (1985).
"Comparacion De Una Tecnica De Deteccion De Antigenos Solubles De *Cisticerus Cellulosae*" by Velasco et al, vol. 25, No. 2, Mar.-Apr. 1983; Salud Publica de Mexico.

*Primary Examiner*—Sidney Marantz
*Attorney, Agent, or Firm*—Oblon, Fisher, Spivak, McClelland & Maier

[57] ABSTRACT

Immunological methods are disclosed for diagnosing active human neurocysticercosis, including a serum test and a cerebrospinal fluid test. The serum test involves detecting an antibody in serum which recognizes at least one of three particular antigens isolated from *Taenia solium* larvae. The cerebrospinal fluid test involves detecting an antigen or antigens of larval origin, preferably by an ELISA technique.

12 Claims, 3 Drawing Sheets

IMMUNOLOGICAL METHODS FOR DIAGNOSING NEUROCYSTICERCOSIS

This is a division, of application Ser. No. 06/766,017, filed Aug. 15, 1985, U.S. Pat. No. 4,740,456.

BACKGROUND OF THE INVENTION

1. Field of the Invention

The present invention relates to immunological methods useful for diagnosing human neurocysticercosis, involving testing for the presence of antigens or antibodies in serum or cerebrospinal fluid (CSF) from a patient to be diagnosed.

2. Discussion of the Background

In many areas of Central and South America, as well as in areas of Africa, Asia and the South Pacific, it is estimated that 3% to 10% of the people in endemic areas are infected with the larvae of *Taenia solium*, a condition referred to as cysticercosis. These larvae are acquired by people who accidentally ingest the eggs of the adult tapeworm. The larvae hatch in the intestine and migrate through the body, becoming imbedded in various tissues and, particularly, in the brain. If the larvae invade the central nervous system (neurocysticercosis), several neurological problems can develop (i.e., migraine headaches, convulsions, loss of memory, numbness of the limbs, blindness, cerebral hypertension). It is not uncommon to find patients with 15 or more larvae in their brains. These larvae are usually about 1 cm. in diameter but can grow to be larger than 5 cm. in diameter.

It has recently been demonstrated that neurocysticercosis, if diagnosed early, can be readily and effectively treated with Praziquantel, a relatively inexpensive antihelminthic drug. This drug should not be used unless a positive diagnosis exists, however, because of toxic side effects. Thus, a reliable diagnosis of neurocysticercosis would be highly desirable for a physician faced with a patient who presents symptoms which may have been brought on by neurocysticercosis. Ultimately, a completely reliable diagnosis of neurocysticercosis requires confirmation of the presence of the larvae in the patient. Current methods of diagnosis are expensive and relatively inaccurate. Physicians in endemic areas who suspect neurocysticercosis on the basis of signs and symptoms depend heavily on CAT scans, if CAT scans are available and if the patient can afford this expensive procedure. In most cases, however, rural clinics and hospitals do not have the radiologic equipment for CAT scans and, at $200 to $300 per CAT scan, most patients cannot afford the procedure. Moreover, it should be emphasized as well that CAT scans cannot discriminate between lesions caused by larvae and other lesions, for example tumors.

Several other methods exist for diagnosis of neurocysticercosis, but each of these methods suffers from some drawback. Laboratory analysis of cerebrospinal fluid (CSF) in neurocysticercosis patients which might lead to diagnosis of this disease has been limited to cytochemical analysis and indirect hemagglutination (IHA). However, cytochemical findings are not specific for neurocysticercosis. Also, positive antibody titers by IHA vary greatly with the clinical presentation of the disease and thus this method is not very reliable.

Recently, enzyme-linked immunosorbent assays (ELISA) have been developed. Mohammad et al. (J. Clin. Microbiol. 20, 775-779, 1984) in a recent study using ELISA for detection of antibodies in serum and CSF of neurocysticercotic patients showed a relative high specificity and sensitivity with this assay (up to 94.7% in CSF from 19 patients). The same authors pointed out that results from ELISA on both CSF and serum in the diagnosis of neurocysticercosis could enhance the reliability of this test. Detection of antibody in serum or cerebrospinal fluid may not indicate that larvae are in the central nervous system since antibody could be in these fluids if larvae are in other parts of the body. To the inventor's knowledge, there have been no reported ELISA studies for the detection of larval *T. solium* antigens in CSF of patients with neurocysticercosis.

Diwan et al. (Am. J. Trop. Med. Hyg. 31, 364-369, 1982) have described an ELISA procedure for the detection of antibodies in the sera of patients with neurocysticercosis which is 79% accurate. Biagi et al. (Revista Medicina Hospital General 25, 501-507, 1961) and Gutierrez-Moctezum (Referata Med. ISSSTE (Mexico), 1, 30-34, 1976) have described indirect immunofluorescent assays (IFA) which are 10%-90% accurate. These tests are disadvantageous because (1) they are technically difficult to perform; (2) they detect only antibody and, therefore, may not indicate an active, current infection, and (3) they do not have high sensitivity.

Other studies have been directed to the characterization of antigens in patients suffering from neurocysticercosis which might be useful in diagnosis of the disease. In Mexico, Velasco et al. (Sal. Publ. Mex. 25, 205-208, 1983) found circulating *T. solium* larval antigens in 77% of 250 CSF samples of neurocysticercosis patients using a latex agglutination test. In the same study, all of the 31 CSF samples from patients in whom cysticercosis was confirmed by surgical exploration were positive for circulating antigens. Following treatment with Praziquantel, additional patients in the same study group were found to have larval antigens in their CSF. This observation suggests that cysticerci within the brain release antigens when patients undergo chemotherapy with Praziquantel. It is important to note that Velasco et al did not characterize the antigenic material at all and referred generally to plural soluble antigens.

Flisser et al. (Clin. and Exp. Immunol. 39, 27-37, 1980), using immunoelectrophoresis, have studied the types of antibodies produced in the sera of individuals affected with neurocysticercosis, using as antigen, a crude extract of cysticerci. They found a total of eight precipitin bands with one, referred to as antigen B, being the most frequently recognized by the sera of cysticercotic patients. This antigen, which induces the production of IgG antibodies, has been successfully purified. It is composed of two protein subunits, differing in their amino acid compositions, with molecular weights of 95,000 and 105,000 daltons, and an isoelectric point between 5.0 and 5.3 (Guerra et al., Cysticercosis: Present State of Knowledge and Perspectives, Flisser et al (eds.), Academic Press, N.Y., 437-451, 1982). To the best of the inventors' knowledge this is the only antigen of the larval stage of *T. solium* which has been characterized in detail. It has not been used in a diagnostic technique for neurocysticercosis.

Although there are several diagnostic techniques available for neurocysticercosis, as described above, each of these methods suffers from some degree of unreliability, and there remains a need for new and improved diagnostic techniques based on the detection of particular antigens or antibodies in body fluids of patients which can lead to more reliable diagnosis of neurocysticercosis. The present inventors have found unexpectedly that antibodies in the serum of patients affected with this disease recognize three particular antigens which can be used for an ELISA-based diagnostic technique of neurocysticercosis which is highly reliable. That these particular three larval antigens could serve as the basis for a highly reliable diagnostic test for cysticercosis is totally unexpected in view of the relative nonspecific diagnostic tests of the prior art. Furthermore, it has also been discovered that there is an antigen in cerebrospinal fluid of patients suffering from this disease whose detection in an ELISA technique can serve as the basis for a highly reliable diagnosis of neurocysticercosis also. No one has yet described an ELISA technique for detecting larval antigens of *T. solium* in CSF of patients with the disease. In consideration of the fact that some antibodies which have been found in the sera of patients may also be found in the sera of persons without the disease, or such antibodies may not be highly correlated with the diagnosis of the disease, it is unpredictable that any test based on the detection of particular antibody or antigen would give as high a reliability as has been observed in the present invention.

SUMMARY OF THE INVENTION

It is therefore an object of the invention to provide a method for serological diagnosis of neurocysticercosis, which involves detection of antibodies in serum by using particular substantially purified *Taenia solium* larval antigens.

It is also an object of the invention to provide another method for diagnosing neurocysticercosis which involves detection of a *Taenia solium* larval antigen present in cerebrospinal fluid of patients affected with neurocysticercosis.

It is yet another object of the invention to provide an ELISA test for detecting either larval antigens in CSF or larval antibodies in serum.

It is yet another object of the invention to identify and describe a method for isolating particular *Taenia solium* larval antigens which are reactive with serum antibodies of patients affected by neurocysticercosis, which antigens are generally not reactive with serum antibodies of patients not affected by neurocysticercosis.

It is a further object of this invention to provide kits for carrying out the diagnostic tests of the invention.

These and other objects of the invention, which will hereinafter become more apparent, have been accomplished by identifying, purifying and characterizing three *Taenia solium* larval antigens having molecular weights of 64K, 53K and 30–32K daltons; also by providing a method for detecting an antigen in cerebrospinal fluid which is useful for giving a highly accurate diagnosis of neurocysticercosis.

DESCRIPTION OF THE PREFERRED EMBODIMENTS

The present invention has as an object the diagnosis of active neurocysticercosis. Two approaches to this object have been employed. The first approach involves a serological diagnostic test for neurocysticercosis. The second approach involves a cerebrospinal fluid diagnostic test for neurocysticercosis. These tests can be used jointly to further enhance the reliability of the diagnosis. It should be noted that both tests involve immunological techniques involving specific binding between antigens and antibodies which are specifically associated with neurocysticercosis and are found in a body fluid of a patient affected with the disease. These two approaches will now be described.

Serological test

In developing a highly reliable serological test for neurocysticercosis, the reactivity profile of *T. solium* antigenic components and serum antibodies of patients affected with neurocysticercosis and control patients was undertaken. As a result of detailed studies, the inventors have found that (A) each patient produced antibodies against a number of larval antigens, (B) all the infected individuals studied had all four classes (IgE, IgG, IgA, IgM) of anticysticercal antibodies at the time serum samples were obtained, (C) there are differences in the number (diversity) and intensity (amount of antigen and concentration of specific antibody) of antigen:antibody reactions as related to the different classes of antibodies present in the patient's sera, i.e. IgG>IgE>IgM>IgA, (D) some degree of similarity was observed in the number and pattern of the bands among patients, (E) the reactivity of antigens varies according to the class of antibody detected, (F) there are both common and antibody-class-specific antigens, (G) certain antigens appeared to be more reactive than others, and (H) there are differences in the frequency with which a particular antigen is recognized by sera of patients.

The percentage of confirmed patients which possessed detectable anti-cysticercal antibodies in the present study (100%) differs from the results reported by Flisser et al. (1980; 44% positive by immunoelectrophoresis) and others (Biagi et al., 1961; Gutierrez-Moctezuma, 1976, 10–90% positive by indirect hemagglutination; and Diwan et al., 1982, 79% positive by ELISA).

Flisser et al. (1980) have reported the presence of cysticercal antigens (antigen H) which seem important in inducing IgE. In conducting the present study the inventors observed a polypeptide (M. W. 81,000) which seems to induce, or at least be recognized, only by IgE antibodies. Various immunological studies have emphasized the prominence of the specific IgE antibody response to parasites (Vervloet et al., Rev. Francais Allergologie 16, 73–78 Clin. Allergy 8, 383–385, 1976; Geller et al., 1978; Ottesen et al., The Lancet 1, 1158–1161, 1979). Since IgE is known to be active in passive cutaneous anaphylaxis, it is of interest to note that the IgE response is highly diversified in patients with cysticercosis. Of 51 cysticercal polypeptides detected in the present study by silver staining (see Examples hereinafter), 37 reacted with sera from patients and 15 of these are recognized by IgE antibodies present in the sera of neurocysticercotic patients.

Guerra et al. (1982) described antigen B (the antigen most commonly recognized by sera of cysticercotic patients) to be composed of two proteins subunits with molecular weights of 105,000 and 95,000 daltons. An analysis of antigenic profiles obtained by the inventors reveals polypeptides with similar molecular weights (95,000) and 115,000). The present inventors also found that the smaller of these antigens (95,000 daltons) reacted with IgG but not IgE whereas the other (M. W. 115,000) reacted with both IgG and IgE. In addition, it is also clear from the present results that antigens with molecular weights of 64,000, 53,000, 45,000, 41,000, 36,000–35,000, 32,000–30,000 daltons are immunodominant. All the patients studied not only had detectable antibodies against them, but these antigens induced the production of more than one class of antibodies (IgG and IgE). The 53,000 daltons antigen also induced IgA. The present inventors have found as well that the IgG, IgE and IgM antibodies recognized the same major polypeptide corresponding to an antigen with a molecular weight of 45,000 daltons. Another major polypeptide with molecular weight 62,000–61,000 daltons was common to IgG and IgE antibodies.

In addition, the inventors have examined the glycoprotein composition of larval antigens and used the specific binding properties of lectins to carbohydrates (Hughes, Membrane Glycoproteins: A Review of Structure and Function, Butterworth and Col, Boston, 135-151, 1976) to further characterize the sugars present in the different antigens (see Examples hereinafter). The importance of the sugar moieties in the immune response against the larval stage of *T. solium* was also evaluated.

Sosa et al. (Life Sciences 21, 1021-1032, 1977) established the carbohydrate content of the glycocalyxlike coat of larvae of *T. solium*, and Lumsden et al. (Cysticercosis: Present State of Knowledge and Perspectives, Flisser et al (eds.), Academic Press, N.Y., 307-361, 1982) comment on the influence of the glycocalyx in the immunogenicity of the worm surface. The data obtained in the present studies suggest the importance of glycopeptides/glycoproteins as antigens. Of the 37 polypeptides detected to be antigenic, 24 had sugar residues recognized by lectins (see Examples hereinafter). On the basis of the different sugar specificities of the lectins tested, the oligosaccharide chains of larval glycoproteins contain N-acetyl-D-glucosamine and alpha-D-galactose. A lectin from wheat germ (WGA) is known to interact with internal 4-O-substituted, 2-acetamido-2-deoxy-Bglucopyranosyl residues (Allen et al, J. Biochem. 131, 155-162, 1973); this is notable because most lectins interact with the nonreducing terminal glycosyl groups of polysaccharide and glycoprotein chain-ends. In contrast, beta-D-galactose, L-fucose, N-acetyl-D-galactosamine and sialic acid were not detectable, thus these sugars appeared to be absent from glycoproteins of larval *T. solium*. However, carbohydrates may be present in the cysticerci but unaccessible on nitrocellulose membranes on which the antigens were bound (see Examples hereinafter).

As a result of detailed studies, the inventors have determined the antigens more frequently recognized by the sera of the patients and the immunoglobulin classes apparently favored in antibody production against each of the larval antigens. Comparative analysis has led to identifying antigens which can be used in the serological diagnosis of cysticercosis. Antigens with molecular weights of 64,000, 53,000, and 32,000–30,000 daltons have been determined to be excellent components of an immunological test for epidemiological surveys as well as serological diagnosis of cysticercosis. It should be noted that the molecular weight of the third antigen is reported as a range since molecular weight determinations of this relatively low size do not permit the accuracy of measurements of higher molecular weights. These three antigens are apparently not recognized by the sera of control individuals (whether from endemic or non-endemic areas) and are, at the same time, identified by the antibodies present in all the patients' sera. These antigens have another advantage of specifically reacting with both IgG and IgE, the two major classes of antibodies against larvae of *T. solium* found in sera of patients. In addition, the antigen of 64,000 daltons is a major antigenic component, easily detectable and found in relatively high concentrations in the antigenic mixture. The fact that the antigen is a glycoprotein readily detectable with a lectin from *Maclura pomifera* (MPA) will facilitate its further isolation and characterization. Another advantage in using these particular antigens is their minimal cross-reactivity.

In its broadest aspect, the present invention encompasses any technique for determining the presence of antibodies in serum which are specifically bindable with the three *Taenia solium* larval antigens described above. Generally, purified antigen will be used to specifically bind the serum antibodies, and then a known technique will be used to detect such binding. Any of the standard immunoassay techniques may be used to detect this binding and hence, the presence of the antibodies. Such techniques include: radioimmunoassays, heterogeneous enzyme immunoassays (e.g., U.S. Pat. No. 3,654,090), heterogeneous fluorescent immunoassays (e.g., U.S. Pat. Nos. 4,201,763; 4,171,311; and 3,992,631), and homogeneous (separation-free) immunoassays.

Homogeneous immunoassays include such techniques as fluorescence quenching or enhancement (e.g., U.S. Pat. No. 4,160,016), fluorescence polarization (J. Exp. Med. 122, 1029 (1965), enzyme substrate-labelled immunoassay (U.S. Pat. No. 4,279,992 and U.K. Patent Spec. No. 1,552,607), prosthetic group-labelled immunoassay (U.S. Pat. No. 4,238,565), enzyme modulator-labelled immunoassay, e.g., using inhibitor labels (U.S. Pat. Nos. 4,134,792 and 4,273,866), enzyme-labelled immunoassay (e.g., U.S. Pat. No., 3,817,837), energy transfer immunoassay (U.S. Pat. No. 3,996,345), chemically-excited fluorescence immunoassay (U.S. Pat. No. 4,238,195) and double antibody steric hindrance immunoassay (U.S. Pat. Nos. 3,935,074 and 3,998,943).

In a preferred embodiment, the first step comprises contacting serum from a human to be diagnosed with at least one of the three substantially purified *Taenia solium* antigens described above. By contacting is meant allowing serum containing antibodies to react in solution with *Taenia solium* larval antigens. The order of addition of these components is not limited. The antigens may be bound to a solid support, such as polymeric beads composed of dextran or other polymeric materials. Preferably, nitrocellulose or cellulose acetate discs are used as a solid support. If a homogeneous (separation-free) immunoassay is utilized to detect the antibodies, a solid support would not be required. Serum is obtained from a person generally by pricking a finger and obtaining whole blood of which serum is a constitu- 
ent. However, the blood may be processed so as to obtain only the serum or plasma portion of the whole blood before contacting with the bound antigens. Moreover, any method for obtaining serum or plasma from a patient may be utilized as long as the antibodies contained therein retain their ability to bind the *T. solium* antigens.

Humans to be diagnosed include those persons presenting symptoms or signs of neurocysticercosis or those persons who, although presenting no overt symptoms of the disease, may have come into contact with the causative agent.

The antigens which are useful for the serological diagnostic test have molecular weights of 64,000, 53,000 or 30,000–32,000. Other properties of these antigens are described above, and below in the Examples.

The three antigens from larval *Taenia solium* may be isolated individually by any standard protein isolation/purification technique. They may be isolated, for example, by an affinity chromatographic technique using antibodies which have been produced against a purified sample of one or more of the antigens. One technique for preparing purified samples of these antigens uses an antigen preparation derived from whole *Taenia solium* cysticerci and subjects this preparation to electrophoresis (SDS-PAGE). This technique is described in the Examples below. It should be noted that the source of whole cysticerci is not specifically limited and may be, for example, any animal infected by the larvae or a non-animal source wherein *T. solium* larvae are grown in vitro. The genes for these antigens could also be cloned in bacteria or yeast and then the gene product could be allowed to accumulate and isolated.

In a preferred embodiment, after isolation and purification, the purified *Taenia solium* antigen is attached to a solid support but other methods not involving a solid support could also be used. The antigens may be bound to any solid support by known techniques. For example, a bi-functional organic molecule may be used to attach the antigen to a solid support. The solid can be made of various plastics, fiberglass, cellulose acetate and nitrocellulose, among others. Preferably, the antigen is attached to a nitrocellulose membrane. After being attached or adhered to the solid support, the antigens can then be cross-linked if desired. If the assay is a homogeneous assay, no solid support would be required. Equivalent techniques allowing separation of a bound from an unbound species without a solid support, such as by precipitation may also be used.

The second step of this embodiment involves contacting the solid support with a detectable antibody. By contacting is meant that a solution of a detectable antibody is allowed to interact with the solid support. By a detectable antibody is meant one which is capable of binding to a human antibody from the serum of the patient which has bound the purified antigen, where the detectable antibody is capable of being detected. More particularly, the detectable antibody can be an anti-human immunoglobulin which is conjugated to a group such as an enzyme which is detectable in the presence of a substrate. Enzyme-conjugated goat or rabbit anti-human antibodies, which have been affinity purified are particularly preferred. These may be obtained commercially or prepared by any known technique. In another particularly preferred embodiment, an anti-human IgG which is gamma chain specific and which is conjugated to an enzyme is used as a detectable antibody. This antibody may be obtained commercially or prepared by a known technique. Use of an affinity-purified, gamma chain specific detectable antibody improves the specificity of the immunological detection of patient antibodies against larval *Taenia solium* antigen. Further, use of this antibody avoids non-specific reaction with other serum components. In general, the detectable group which is conjugated to the detectable antibody may be any enzyme or other detectable species which has been developed for immunoassays. For example, enzymes, fluorescent groups, radioactive groups and others could be used. The enzyme peroxidase is particularly preferred. Peroxidaseconjugated affinity purified antisera such as goat anti-human IgG ($F_c$-fragment chain specific) may be obtained commercially at the present time from Cappel Laboratories, Cochranville, PA. When peroxidase is the the detectable group conjugated to the detectable antibody, a substrate such as 4-chloro-1-naphthol may be used for detection of the detectable antibody.

By detecting the detectable antibody that has reacted with the human antibodies, is meant that the detectable group which is conjugated to the detectable antibody is treated or manipulated so as to determine its presence. For example, if an enzyme such as peroxidase is conjugated to the antibody, the detecting step would involve adding a peroxidase substrate such as 4-chloro-1-naphthol to the bound antibody and observing a color change as peroxidase catalyzes conversion of the substrate to a colored species. In the case of other enzymes, such as alkaline phosphatase, β-D-galactosidase, and horseradish peroxidase, other substrates may be used. The substrate to be used should be chosen such that after the enzyme catalyzes a chemical conversion of the substrate to a product, a change which is observable to a person employing this test should result. Substrates such as p-nitrophenyl phosphate or 3,3'-diamino-benzidine may be used as substrates. Other detectable groups may also be conjugated to the antibody.

A kit containing the required components for carrying out a diagnostic test for neurocysticercosis based on detection of serum antibodies can be assembled. The kit can contain purified *T. solium* larval antigen coated on a solid support such as a nitrocelluloe or cellulose acetate disc, and a container of a detectable antibody conjugate which is capable of binding antibody from the serum of a patient which is bound to the purified larval antigen. An ELISA test is most preferred for the kit since it lends itself to a readily detectable positive or negative diagnosis. Thus, the kit should also contain a container of a substrate which is reactive with an enzyme which is conjugated to the detectable antibody, the substrate being readily detectable after reaction with the enzyme. Finally, the kit will generally contain a positive control (such as a support having pre-coated thereon antibody reactive with the *T. solium* larval antigen or a support having coated thereon only the enzyme employed in the ELISA) and a negative control (an untreated support). Blood obtained by a finger prick would generally be used as the fluid to be tested for the presence of *T. solium* larval antibodies and the kit may optionally contain means for obtaining blood from a patient, such as a syringe or sharp instrument designed for venipuncture.

Cerebrospinal Fluid Test (CSF)

The inventors have discovered that there is a single principal *T. solium* larval antigen present in cerebrospinal fluid and that this antigen may be detected in an ELISA technique which may be used to diagnose neurocysticercosis with high reliability. Based on test results, all patients with surgically and histologically confirmed infections were found to have the antigen in their CSF as determined by this technique (see the Examples below for more detailed information on these tests). A correlation this high (100%) based on surgical/histological confirmation has not been achieved before by an ELISA technique for this disease. Mohammad (J. Clin. Microbiol., 20 775-779) achieved a level of 94.7% in CSF using an ELISA technique to detect antibodies in serum and CSF. It should be noted that the present test detects an antigen in CSF rather than an antibody.

Several factors were considered in the development of the CSF assay of this invention. Among these factors was the attachment of antigens onto solid phases (Lehtonen et al., J. Immunol. Meth. 34, 61-70, 1980). Antigen cross-linking has been useful in increasing the binding of relevant antigens present in crude antigen extracts (Rotmans et al., J. Immunol. Meth. 70, 53-64, 1984). In a preferred embodiment of the present invention, antigen cross-linking may be used to enable use of minimal amounts of *T. solium* antigen extract. This procedure increases the sensitivity of the ELISA when detecting IgG antibodies in CSF in dilutions as high as 1/5,120. The same procedure allowed cross-linking of the proteins present in CSF, thus promoting the binding of larval antigens which can be detected in CSF dilutions as high as 1/320.

The first step of a preferred method for diagnosing human neurocysticercosis using cerebrospinal fluid involves contacting cerebrospinal fluid from a human to be diagnosed with a solid support which is capable of binding any *T. solium* larval antigen present in the cerebrospinal fluid. By contacting is meant that the cerebrospinal fluid is placed on the solid support. The cerebrospinal fluid may be obtained by known methods and may involve a lumbar spinal tap. The humans to be diagnosed are persons who present signs or symptoms of neurocysticercosis or are those persons who may have come into contact with the causative agent. The solid support can be any support which is capable of binding the antigen present in cerebrospinal fluid, such as nitrocellulose membranes or cellulose acetate membranes, nylon, plastic, fiberglass and others.

The next step of this invention involves contacting the support with a first antibody, where the first antibody is bindable with a larval *T. solium* antigen which may be found in cerebrospinal fluid. The first antibody may be induced by any known technique starting with either crude *T. solium* extracts or purified antigen. Numerous texts are available describing the fundamental aspects of inducing antibody formation; for example reference may be made to Parker, *Radioimmunoassay of Biologically Active Compounds,* Prentice-Hall (Englewood Clifts, N.J., USA 1976). In the usual case, a host animal such as a rabbit, goat, mouse, guinea pig, or horse is injected at one or more of a variety of sites with the crude antigen extract or a purified immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps such as affinity chromatography using purified antigen may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas,* Meclers et al., eds., Springer-Verlag (New York 1978), Nature, 266, 495 (1977), *Science,* 108, 692 (1980), and Methods in Enzymology, 73 (Part B); 3-46), (1981).

An example of a particular method of preparing the first antibody in the form of an antiserum useful in the present invention may be found in the Examples.

The next step of this invention involves contacting the solid support with a second antibody, where the second antibody is bindable to the first antibody and the second antibody is also conjugated to a detectable group. The detectable second antibody should be an antibody which reacts with the first such as affinity-purified enzyme-conjugated goat or horse antibodies. These may be obtained commercially or prepared by known methods. The second antibody is generally conjugated with an enzyme which is capable of interacting with a substrate to produce an observable species. However, other detectable groups such as fluorescent moieties or radioactive moieties may also be conjugated to the second antibody to allow detection.

In another embodiment of this invention, instead of utilizing a detectable second antibody for detecting binding of the first antibody to the larval antigen in cerebrospinal fluid, the first antibody is conjugated to at least one biotin molecule, and enzyme-conjugated avidin is used to detect binding of the first antibody to the antigen. Biotin may be conjugated to the first antibody by known techniques. See, for example, J. Immunol. Meth. 48, 299. Avidin may be conjugated to any known detectable species developed for use in an immunoassay, but an enzyme such as peroxidase is generally preferred. After the avidin conjugate is added to the biotinylated first antibody bound to CSF antigen, the detectable group is detected. If peroxidase is the detectable group attached to avidin, a peroxidase substrate is utilized. Alternatively, avidin can be conjugated to the first antibody and detectable group-conjugated biotin may be used for detection.

Detection of the *T. solium* larval antigen in CSF is preferably carried out by an ELISA technique. Microtiter plates can be used as a support for larval antigens from CSF. These plates are preferably treated so that the antigen is cross-linked (this is referred to above and in an Example included hereinafter). Cross-linking of the antigen is useful in increasing binding of antigens present in crude antigen extracts (see J. Immunol. Meth. 70, 53-64).

The ELISA technique is preferably carried out by contacting CSF from a person to be diagnosed with the solid support described above, then adding a first antibody which is capable of binding the *Taenia solium* antigen from CSF. As referred to above, this first antibody may be an antiserum against a crude *T. solium* extract or, preferably, it may be a purified antibody capable of specifically binding the CSF antigen. This first antibody may also be biotinylated in one embodiment of the invention. Next, a detectable group conjugated second antibody capable of binding the first antibody or detectable group conjugated avidin is added. In a preferred embodiment, the second antibody or avidin is conjugated to peroxidase.

The ELISA procedure proposed can be used to determine the number and/or biomass of larvae in each patient by determining the concentration of antigen in cerebrospinal fluid. This information would be useful in determining the timing and dosages of immunosuppressive agents to control potentially life-threatening inflammatory responses leading to cerebral hypertension. In addition, the success of therapy in eliminating all larvae in patients can be monitored by examining cerebrospinal fluid after completion of therapy to assure that no living larvae remain. If larval antigens are detected in the cerebrospinal fluid following therapy, the patients should undergo additional treatment to completely eliminate the larvae and effect total cure.

The following is a general description of one embodiment of this aspect of the present invention:

Rabbits are immunized with a crude extract of larvae of *Taenia solium* and the resultant antiserum collected. Cerebrospinal fluid from patients confirmed to have neurocysticercosis or from uninfected persons is obtained. A small quantity of the various samples of cerebrospinal fluid is placed in 96-well plates and allowed to adhere to the plates. Next, rabbit antiserum against larvae is added to the plates and antibodies in this serum bind to antigens of the parasite which may be present in the cerebrospinal fluid. After this reaction, the plates are washed thoroughly with buffer and a peroxidase-labeled antibody against the rabbit antibodies is added. Following incubation and washing, substrate (4-chloro-1-naphthol) is added and the presence of antigens of larvae of *T. solium* is detected in the cerebrospinal fluid of confirmed patients but not in the control samples.

A kit containing the required components for carrying out a diagnostic test for neurocysticercosis based on detection of the CSF antigen can be assembled. The kit includes a container of an antibody or antiserum which can bind the *T. solium* larval antibody, and a means for determining if such binding occurs upon contacting cerebrospinal fluid from a patient to be diagnosed. A preferred embodiment of such a kit and its use is described as follows:

An attending physician would remove a sample of spinal fluid from the patient by a known technique, place a small sample of this fluid on a nitrocellulose disc, which can be marked "Patient". A second disc would have an antigen of larvae already on it as a positive control, and a third disc would remain as a negative control. All three discs would next receive a small sample of the rabbit anti-larval antiserum, would be allowed to incubate for 15-30 minutes at room temperature and then washed with buffer by immersion. The peroxidase-labeled goat anti-rabbit serum is then added, incubated, washed and the substrate (4-chloro-1-naphthol) added. After 15 minutes the three discs are examined. The negative control should remain colorless, the positive control would be intensely colored, and the patient's sample if colored would indicate infection and if not colored would indicate no infection with larvae.

The kit may also further comprise medical instruments which may be used to extract cerebrospinal fluid from a human to be diagnosed. Such instruments can comprise a needle or syringe and a local anesthetic or other medical instruments which are useful for such withdrawal.

The kit can also contain biotinylated first antibody instead of unconjugated first antibody, and enzyme-conjugated avidin instead of enzyme-conjugated second antibody.

An ELISA technique using biotinylated first antibody, avidin-conjugated peroxidase, and 4-chloro-1-naphthol represent the best mode of this aspect of the invention contemplated by the inventors at the present time.

The invention will be better understood by reference to certain specific examples which are included herein for purposes of illustration only and are not intended to be limiting of the invention or any embodiment thereof, unless specified.

EXAMPLES

SERODIAGNOSTIC TEST

Preparation of Taenia solium cysticercal antigen extracts

Whole *T. solium* cysticerci were excised from the skeletal muscle of two naturally infected pigs, (special care was taken to remove the larvae clear of host tissue) and washed extensively in cold Dulbecco's phosphate buffered saline (PBS; pH 7.4), containing enzyme inhibitors (100 U/ml aprotinin 2 mM pepstatin A and 2 mM phenylmethylsulfonylfluoride (PMSF; Sigma Chemical Co., St. Louis, Mo). Washed larvae were resuspended in one volume of PBS containing enzyme inhibitors, and homogenized at 0° C. by at least 100 strokes of a tight fitting Dounce homogenizer. The homogenates were further disrupted by sonication on ice, using a Biosonik III sonicator (Rochester, NY), 6 times for a total of 3 min. at 20 kHz with 30 second cooling intervals. The sonicates were then centrifuged at 25,000 xg for 1 hour at 4° C. to remove cellular debris. The supernatant fluid (antigen extract) was dialyzed against distilled water and concentrated using Aquacide II-A (Calbiochem-Behring Corp., La Jolla, CA), after which the concentration of protein was adjusted to 10 mg/ml (Bradford, Anal. Biochem. 72, 248-254, 1976). The antigenic extracts were stored at $-70°$ C. in 50 $\mu$l aliquots until used. Since cysticerci have been shown to absorb host serum proteins, normal swine serum and uninfected swine tissue were used as control antigens. The crude extract of swine tissue was prepared as described for *T. solium* larvae; normal serum was obtained from Cappel Laboratories, Inc. (Cochranville, PA).

Sodium dodecyl sulfate-polyacrylamide gel electrophoresis (SDS-PAGE)

All reagents were obtained from Bio-Rad (Richmond, CA). Prior to electrophoresis each antigen preparation was mixed with an equal volume of sample buffer (0.08M Tris-HCl), pH 6.8, 0.1M dithiothreitol, 2% SDS, 10% glycerol, and 0.2% bromophenol blue) after which this mixture was heated at 100° C. for 2 min. A 120 $\mu$l sample (1.2 mg of protein)/single well in preparative gels or 10 $\mu$l samples (100 $\mu$g of protein)/well in the multiple well gels were used for electrophoresis. SDS-PAGE was conducted in 12.5% polyacrylamide resolving gels (5% stacking gel) containing 1% SDS. High and low molecular weight markers were included in each run. Electrophoresis was performed with the use of the discontinuous SDS buffer system described by Laemmli (Nature (London) 227, 680-685, 1970) at 16° C. at 8 watts and set at constant wattage until the bromophenol blue reached the bottom of the gel. Resolved proteins were then either transferred to nitrocellulose membranes or stained with Coomassie blue or silver stain as described by Morrissey (Anal. Biochem. 117, 307–310, 1981). High and low molecular weight markers (Bio-Rad Laboratories, Richmond, CA) were included in each run.

Figure 1:
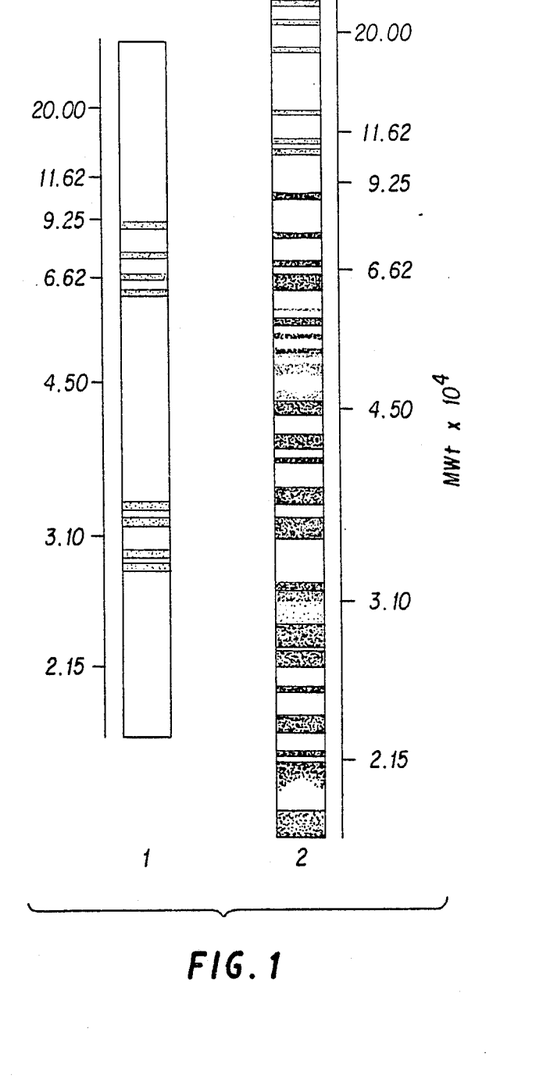
FIG. 1 shows detection of polypeptide components of larval *T. solium* by silver staining (column 2) and those detected by amido black after electroblotting to nitrocellulose membranes (column 1).

FIG. 1 illustrates the polypeptide composition of the larval stage of *T. solium* when analyzed by SDS-PAGE and silver staining. As shown, 51 bands ranging from $1.35 \times 10^4$ to $2.6 \times 10^5$ daltons were detected after staining.

Electrophoretic transfer of larval components to unmodified nitrocellulose: Western blotting Antigenic extracts previously resolved by electrophoresis were transferred to nitrocellulose membranes (Bio-Rad, Richmond, CA) using a Bio-Rad Trans-Blot cell as described by Grogl and Kuhn (J. Parasitol., in press, 1984). Briefly, the polyacrylamide slab gels were washed sequentially with 300 mls. of 1.0%, 0.5% and 0.1% Triton X-100 in transfer buffer (25 mM Tris, pH 8.3, 192 mM glycine/20% (v/v) methanol) for 15 min. each, to partially remove SDS. Nitrocellulose membranes were equilibrated in transfer buffer before use. Electrophoresis was performed at 60 V (0.21A) for 12 h at 4° C. in transfer buffer, using a magnetic stirrer to assure continuous mixing of the buffer. The membranes were then cut into strips for use in the various experiments. Control blots were stained with amide black following the method of Towbin et al. (J. Immunol. Meth. 72, 313–340, 1979). Under these conditions transfers were quantitative and reproducible over a wide range of molecular weights.

Of the 51 polypeptides detected by SDS-PAGE and silver staining, 39 were detected, after transfer, by staining the nitrocellulose membranes with amide black. The molecular weight range of the larval components was identical to that of the polypeptides detected on the gels. Differences in the number of polypeptides observable after transfer is probably due to the lower sensitivity of the amido black staining method.

Test sera

Sera were tested from seventeen individuals with neurocysticercosis, diagnosed by a combination of clinical syndromes, positive serology, and positive computerized axial tomographic (CAT) brain scans obtained from patients from different areas in Colombia, South America. Negative control sera were obtained from eight healthy North American adults, who had never traveled outside of the United States, and from seven healthy Colombians (sero-negative). Results obtained from only five of the control sera and five of the sera from neurocysticercotic patients will be described in detail (below) with brief general comments regarding results using the other sera (see Table I for details). All comments regarding control sera or sera from patients will refer only to the five of each group studied in detail.

Enzyme-linked immunodetection of larval antigens bound to nitrocellulose membranes Following transfer of antigens, the nitrocellulose membranes were blocked with 3% (w/v) bovine serum albumin (BSA, fraction V, Sigma Chemical Co., St. Louis, Mo.) and 3% (v/v) normal goat serum in PBS (pH 7.4) containing 0.1% Tween-20 (Sigma Chem. Co.) at 37° C. for 2 h on a rocking platform. The nitrocellulose membranes were then washed three times over a 30 min. period with PBS, 0.05% Tween-20, after which they were immersed in control serum or serum samples from patients with neurocysticercosis at a dilution of 1/30 in PBS containing 10% (v/v) fetal bovine serum (GIBCO, Grand Island, N.Y.). Binding was allowed to occur overnight at 28° C. with gentle shaking. The nitrocellulose membranes were washed again as before, and incubated for 1 hr. at 28° C. with one of the following horseradish peroxidase-conjugated, affinitypurified antisera: (a) the IgG fraction of goat antihuman immunoglobulins (IgA, IgG and IgM heavy and light chains specific), (b) goat anti-human IgG (Fc-fragment, gamma chain specific), (c) goat anti-human IgM (Mu chain specific), (d) sheep anti-human serum IgA (alpha chain specific), and (e) the IgG fraction of goat antihuman IgE (epsilon chain specific; all from Cappel Laboratories, Cochranville, PA) at their respective optimal dilutions in PBS. After washing, the strips were rinsed in 0.05M Tris-0.25M NaCl buffer (pH 7.5) and incubated with the substrate solution (0.05% 4-chloro-1-naphthol, 60 mg in 20 ml of cold methanol added to 100 ml Tris-saline buffer containing a final concentration of 0.015% $H_2O_2$; Sigma Chem. Co.). The membranes were incubated form 10–20 min. until color developed and the reaction was stopped by washing in deionized water and drying the membranes between two sheets of filter paper, after which they were photographed. The highest sensitivity of the reaction and the most intense color development was obtained when both the first and second antibodies were used in a concentration high enough to saturate binding sites. Because the antibody protein of different preparations varies, and the percentage of active antibody and potency of the anti-immunoglobulin conjugates can vary considerably, the various antibody preparations were titrated in an enzyme-linked immunosorbant assay (ELISA) using larval antigens to optimize each system (Voller et al., J. Clin. Path. 29, 150–153, 1976). The optimal working dilution of the conjugates ranged from 1/200-1/1000. A detection limit of 0.1 ng of Ig was determined for the assay without observing an increase in the background of the strips or compromising the specificity of the reactions.

Controls included reactions on membranes to which larval components were bound (a) in the absence of test sera (i.e., serum from healthy, uninfected controls or infected individuals), incubated with the differnt horseradish peroxidase-conjugated, affinity purified anti-human antisera and substrate, (b) in the presence of test sera and substrate, but no second (anti-human) antibody, or (c) in the presence of substrate only. These controls and those using normal swine serum and the crude extract of uninfected swine tissue as antigens were uniformly negative.

Larval antigens identified by antibodies in normal sera

In general, sera from Colombian controls detected a higher number of antigens than sera of the North Americans. No antigen was deteted using sera from American controls, that was not recognized by the sera of the Colombian controls. A band with a molecular weight of 62,000 daltons was consistently detected by the sera of three control individuals, independent of the class of antibody under study. In addition, other very faint bands with molecular weights of approximately 95,000, 49,000, 45,000, 41,000 and 36,000 daltons were recognized by control sera. The highest degree of reactivity was exhibited by control No. 1, whose serum detected each of the antigens cited above when an IgG fraction of goat anti-human immunoglobulins (IgA, IgG and IgM heavy and light chains specific) was used as indicator antibody (see FIG. 2).

Larval antigens identified by antibodies in the sera of patients

Figure 2:
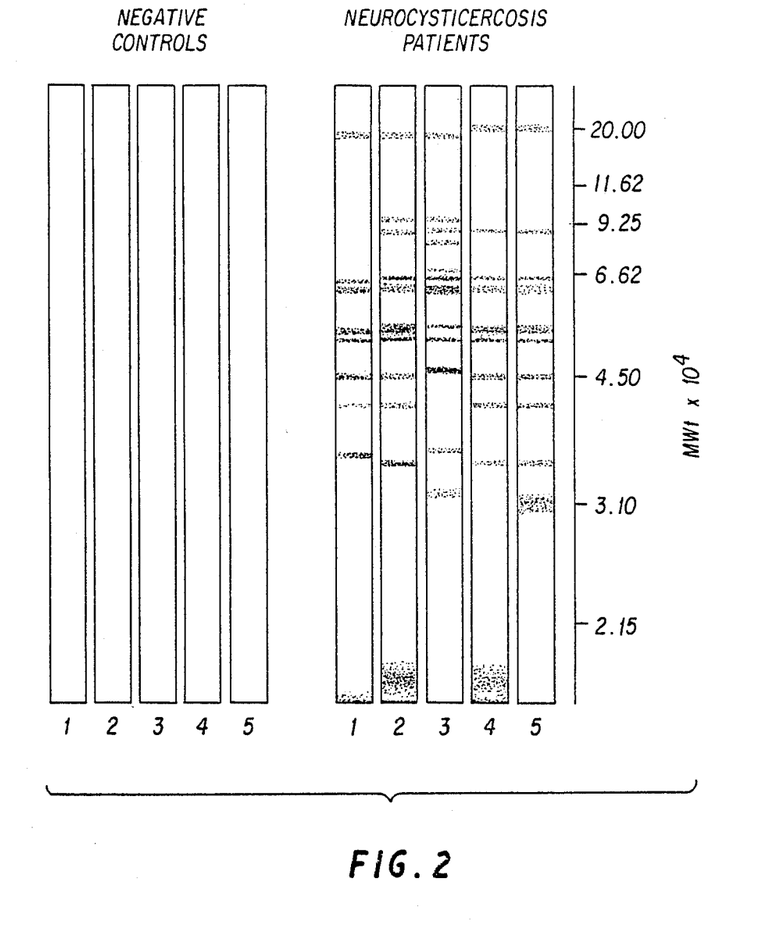
FIG. 2 shows components of larval *T. solium* reactive with sera of five negative controls (1, 2 and 3 are from North Americans and 4 and 5 are from Colombians) and five patients with neurocysticercosis. Peroxidase-labeled, goat antihuman IgG, IgA and IgM (heavy and light chains) was used as indicator antibody.

FIG. 2 shows the reactivity profile of total immunoglobulins present in the sera of five patients against the larval extract. A total of 37 different antigenic bands with apparent molecular weights of 260,000–14,000 daltons were identified. Each of the positive sera identified between 17–35 antigens. Twelve antigenic bands of molecular weights 200,000, 95,000, 90,000, 64,000, 62,000, 53,000, 49,000, 45,000, 41,000, 39,000, 36,000 and 31,000 daltons were recognized by all of the positive sera. The most highly reactive bands with molecular weights of 200,000, 64,000, 62,000, 53,000, 49,000, 45,000, 36,000, and 16,000 were found in 4 of the five patients' sera.

Larval antigens identified by IgG antibodies of patients

Figure 3:
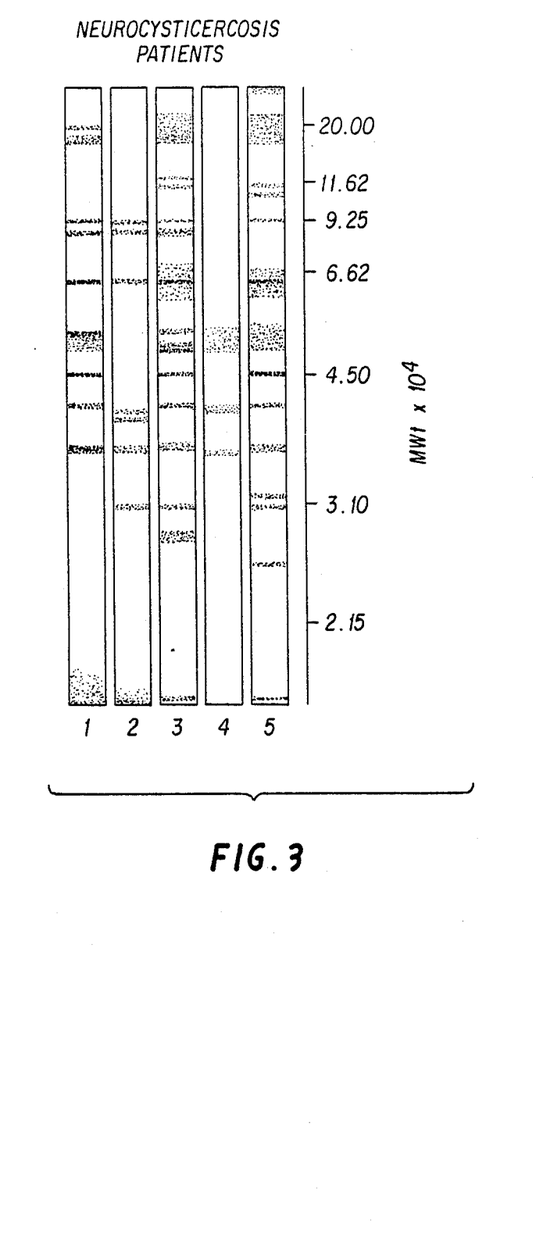
FIG. 3 shows components of larval *T. solium* reactive with IgG antibodies of patients with neurocysticercosis.

As shown in FIG. 3, an analysis of the reactions obtained with IgG antibodies of patients against larval antigens revealed a total of 34 parasite-specific components as being antigenic, ranging in molecular weights from 250,000–14,000 daltons. Seven major polypeptides with molecular weights of about 64,000, 62,000, 53,000, 49,000, 45,000, 36,000, and 14,000 were recognized by at least three of the five patients' sera. Each of the positive sera recognized between 12 and 32 antigens. Eight antigenic bands with molecular weights of approximately 64,000, 53,000, 49,000, 45,000, 41,000, 35,000, 30,000 and 25,000 daltons were identified by all of the patients' sera. Differences in the banding pattern between the IgG-reactive antigens and the other immunoglobulin classes were observed especially in the higher (250,000–145,000 daltons) and lower (29,000–14,000 daltons) molecular weight ranges (see below). After comparison, 7 high molecular weight components (antigens with molecular weights of 250,000, 235,000, 228,000, 215,000, 200,000, 175,000 and 153,000) and five low molecular weight antigens (with molecular weights of 26,000, 25,000, 23,000, 20,000 and 14,000) seem to be IgG-class specific. In addition, an intensely stained band with a molecular weight of 92,000 daltons was observed to be detected exclusively by IgG antibodies.

Larval antigens identified by IgM antibodies of patients

Results from the antigenic analysis of larval antigens recognized by IgM antibodies revealed 7 components with molecular weights of 77,000–41,000 daltons. The most intensely stained band had a molecular weight of about 45,000 daltons. However, only two of the five patients recognized this band. Another band with an apparent molecular weight of 48,000 daltons, although less intensely stained than the 45,000 dalton band but more intensely stained than the rest of the bands, was recognized by all of the five patients' sera. Each of the positive sera identified between 1 and 6 antigens, with the 48,000 dalton molecular weight antigen the only component recognized by all of the five immune sera. The component with a molecular weight of 77,000 daltons appears to be recognized exclusively by IgM antibodies.

Larval antigens identified by IgE antibodies of patients

A total of 15 polypeptides, ranging in molecular weights from 115,000–29,000 daltons were identified as being antigenic. The most intensely stained bands observed in the patterns obtained with IgE antibodies had approximate molecular weights of 61,000 and 45,000 daltons. These major bands were detected by all of the tested sera. Each of the 5 sera from neurocysticercotic patients recognized between 11-15 antigens. Eleven antigens with apparent molecular weights of 115,000, 110,000, 64,000, 61,000, 53,000, 45,000, 41,000, 39,000, 36,000, 32,000, and 29,000 daltons were recognized by all of the positive sera. A very faint band recognized by at least 3 of the 5 sera, corresponding to an antigen with a molecular weight of 81,000 daltons, appeared to be IgE class specific. However, IgG antibodies present in the sera of patient No. 5 (FIG. 3) reacted to a similar band of 80,000 daltons.

Larval antigens identified by IgA antibodies of patients

Results from the analysis of the larval antigens recognized by IgA antibodies show that, in general, very weak reactions of IgA antibodies to larval antigens were observed. A total of 6 different bands ranging in molecular weights from 72,000–36,000 daltons were identified as being antigenic. Each of the 5 immune sera tested recognized 3–5 antigens, of which antigens those of 60,000 and 53,000 daltons were recognized by all five positive sera.

Reactions observed with sera of other patients

Sera of 12 other patients were examined using anti-total Ig as the indicator antibody and no additional antigens were identified that were not also found on analysis of the individual reactivity of isotypes of the five patients described above.

Detection of larval components which bind lectins after SDS-PAGE and Western blotting Binding of lectin to polypeptides was detected according to a modification of the method developed by Hawkes (Anal. Biochem. 123, 143–146, 1982). After transferring larval components to nitrocellulose membranes, the membranes were blocked with 0.2% Tween20 in PBS alone (without BSA) for 1 hr. at room temperature (Batteiger et al., J. Immol. Meth. 55, 297–307, 1982). BSA (fraction V, Sigma) was not used because it is known to contain glycoprotein impurities (Glss et al., Anal. Biochem. 115, 219–224, 1981). Nitrocellulose membranes were incubated for 2 hr. at room temperature with one of the following peroxidaselabeled lectins: *Dolichos biflorus* agglutinin (horse gram-DBA), *Ulex europaeus* agglutinin (UEA-I), *Limulus polyphemus* (horseshoe crab-LPA), *Maclura pomifera* (osage orange-MPA), *Arachis hypogaea* (peanut agglutinin-PNA), *Triticum vulgaris* (wheat germ agglutinin-WGA), *Glycine max* (soybean agglutinin-SBA) and *Ricinus communis* I (castor bean-RCA-I; all from E.Y. Laboratories Inc., San Mateo, CA.) Each lectin was supplied by the vendor in different solvents. Therefore, when used, each lectin was diluted in the same solvent in which it was supplied to a final concentration of 200 μg/ml. Reactions of all the lectins were controlled by inclusion of specific competing sugars at a final concentration of 0.2M in the incubation mixtures. Thus, the following sugars (purchased from Sigma Chemical Co. or E.Y. Laboratories were used as competitors: beta-D-galactose, (beta-D-Gal), alpha-L-fucose (alpha-L-Fuc), N-acetyneuraminic acid (NANA), N-acetyl-D-glucosamine (D-GlcNAc), alpha-D-galactose (alpha-D-Gal) and N-acetyl-D-galactosamine (D-GalNAc). Detection of the bound peroxidase labeled lectins was accomplished by incubating the membranes for 10-20 min. in a fresh preparation of 4-chloro-1-naphthol as described above. It was determined that free peroxidase did not bind to the transferred larval components.

Identification of carbohydrate-containing larval components by lectins

Of the lectins tested, DBA, UEA-I, LPA, PNA, SBA and RCA-I failed to label any larval glycopeptides specifically. Lectins from *Triticum vulgaris* (WGA) and *Maclura pomifera* (MPA) specifically labeled glycopeptides over a wide range of molecular weights (115,000-36,000 daltons and 230,000-29,000 daltons, respectively). A total of 21 glycopeptides were labeled with MPA, while fewer, 14 glycopeptides, were specifically labeled with WGA. Glycopeptides with apparent molecular weights of 115,000, 105,000, 53,000, 49,000, 45,000, 41,000, 39,000 and 36,000 daltons were identified by both lectins. Five of these glycopeptides, i.e., components with molecular weights of 53,000, 49,000, 45,000, 39,000 and 36,000 daltons, were recognized as major antigenic components by the antibodies present in the sera of cysticercotic patients. With the exception of the 49,000 and 39,000 daltons antigens, each of these glycopeptides was recognized by at least three of the four classes of antibodies studied, i.e., antibodies of the IgG, IgE and IgA class. The binding of the lectins WGA and MPA was inhibited or markedly reduced when their specific competing sugars, N-acetylglucosamine and alpha-D-galactose were included in the incubations.

Periodate Oxidation of Larval Components

Results described in the above Examples indicate that a significant number of carbohydrate-containing substances of larvae are immunoreactive in infected hosts. To confirm these observations, and to determine the degree of involvement of the carbohydrate portion in the antigenicity of these components, we considered it of interest to determine the effect of pretreatment of these components with $NaIO_4$ on the reactivity with anti-cysticercal antibodies from patients.

Cleaving of carbohydrate moieties of the different larval components was carried out by oxidation using a modified version of the Rothfus and Smith (J. Biol. Chem. 238, 1402-1410, 1963) technique. Briefly, nitrocellulose membranes to which larval components had been transferred were treated with 10 mM $NaIO_4$ in 50 mM sodium carbonate buffer (pH 8.1) for 1 hr. at 37° C. in the dark. The reaction was stopped by extensively washing the strips in PBS containing 0.1% Tween-20. Untreated, and $NaIO_4$-treated membranes were run in parallel. After treatment with $NaIO_4$, reactivity against bands corresponding to molecular weights of about 115,000, 95,000, 81,000, 39,000, 36,000 and 32,000 daltons were completely abolished.

Cerebrospinal Fluid Antigen Diagnostic Test

The preparation of antigenic extract from larval *T. sodium* was the same as described in the serological diagnostic test (above).

Subjects and test samples

Soon after admission, CSF samples were obtained from sixteen hospitalized patients with presumptive diagnosis of neurocysticercosis who were treated at the Neurology and Neurosurgery Department at the University Hospital of the Antioquia University Medical School in Medellin, Colombia. Specimens were obtained by lumbar puncture using standard techniques. The diagnosis of neurocysticercosis was based upon the following criteria: epidemiological information, neurological signs and symptons, simple and contrast CT scanning suggestive of cerebral cysticercosis (Byrd et al. Radiology 144, 819-823, 1982; Botero and Castano Am. J. Trop. Med. Hyg. 31, 810-821, 1982), and in nine of the sixteen patients, detection of antibodies (titer $\geq 1/128$) against larval antigens of *T. solium* in serum or CSF by IHA. In four of the sixteen patients the diagnosis was confirmed by histological examination of the lesion following surgery (see Table 2 for details).

CSF samples used as controls were obtained from patients suffering from neurological disorders other than neurocysticercosis. These samples were from three patients with proven tuberculosis meningitis, two with endocranial trauma and one with multiple myeloma. Also used as controls were CSF samples from nine patients without any signs or symptoms of neurological disease. These samples were obtained at the same institution during spinal anesthesia for urological, gynecological or orthopedic operations.

Rabbit antiserum

Three New Zealand white female rabbits were immunized with the larval antigen extract. Each rabbit was given three iummunizations at monthly intervals. The first immunization consists of 1 mg of antigen in 1 ml of sterile PBS mixed with an equal volume of Freund's incomplete adjuvant, administered intradermally in ten different sites. The second and third doses of 1 mg of antigen (in 1 ml of sterile PBS) were given intravenously. Blood was collected by venipuncture before immunization and seven days after the second and third doses. A pool of this immune rabbit sera was used as antiserum after being tested for antibody reactivity by ELISA. Sera from rabbits obtained prior to immunization were used as controls.

ELISA reagents

The optimal dilutions of reagents were determined as described by Voller et al. (Bull. World Health Org. 53, 55-65, 1976). All washing procedures were performed five times with PBS. The dilution buffer for all ELISA tests was prepared as follows: 0.3M Tris, 0.3M NaCl (pH 7.6); 5% (w/v) bovine serum albumin (Fraction V, Sigma Chem. Co.) and 0.5% Triton X-100 (Sigma). Tris-citrate buffer (0.3M Tris-base with 0.5% Triton X-100, pH adjusted to 6.0 by addition of anhydrous citric acid) was used for preparing the substrate solution of 0.3% (w/v) ortho-phenylene diamine (Sigma) and 0.025% $H_2O_2$. $H_3OP_4 \cdot HCl$ solution (0.1M $H_3PO_4$, HPLC grade; 0.1M HCl) was used to stop the ELISA reaction. The following horseradish peroxidaseconjugated, affinity-purified second antibodies were used: The IgG fraction of goat anti-human IgG (gamma chain specific), goat anti-human IgM (Mu chain specific), and goat anti-rabbit IgG (heavy and light chains specific). These second antibodies were obtained from Cappel Laboratories (Cochranville, PA).

Modification of microtiter plates for antigen crosslinking linking

Polyvinylchloride microtiter plates (U-bottom wells, Falcon 3911) were treated with poly-D-lysine hydrobromide and glutaraldehyde (Sigma Chemical Co.) to increase the binding of either larval antigens or antigens present in CSF. The 96 wells of the microtiter plates were filled with 100 μl of poly-D-lysine solution (15 μg/ml of 0.1M sodium bicarbonate buffer, pH 9.6) for 2 h at 37° C. After washing the plates with PBS, the wells were filled with 100 μl of a solution containing 0.5% (v/v) glutaraldehyde in PBS. After an incubation of 30 min. at 37° C. the plates were washed with PBS and stored at 4° C. until further use.

ELISA for the detection of antigen of T. solium larvae in CSF

Two-fold serial dilutions of CSF in sodium bicarbonate buffer (beginning with 1/20 dilution) were placed into duplicate wells of the modified microtiter plates (100 μl/well). The plates were incubated at 37° C. for 2 h and then washed with PBS. 100 μl of rabbit antiserum (1/500 in dilution buffer) were then added to all wells and incubated for 1 h at 37° C., after which the plates were washed with PBS. Next, 100 μl of goat anti-rabbit second antibody (1/1000 in dilution buffer) were added to all wells, and after incubation for 1 h at 37° C., the plates were washed with PBS. The substrate solution was then added (100 μl/ well) and after 30 min. incubation at 37° C., the reaction was stopped by adding $H_3PO_4$-HCl solution (50 μl/well). To obtain quantitative readings, the optical density of the reactants was measured at 490 nm on a Biotek ELISA reader (Burlington, VT). For each of the microtiter plates, control wells coated with dilution buffer instead of CSF samples, were prepared. The ELISA readings obtained from these wells, when incubated with rabbit antiserum, were used as background controls.

ELISA for the detection of anti-larval antibodies in CSF

The wells of the modified microtiter plates were filled with 100 μl of sodium bicarbonate buffer containing antigen extract of T. solium larvae (10 μgMl. The plates were incubated for 1 h, at 37° C., and then for 8 h at room temperature. The plates were then washed with PBS and either used immediately in the ELISA, or stored at 4° C.

Four-fold serial dilutions of CSF samples (100 μl/well, starting with a 1/20 dilution) were prepared in dilution buffer and placed in duplicate wells of the antigen-coated microtiter plates. The plates were incubated at 37° C. for 1 h, washed with PBS, and 100 μl of peroxidase-labeled anti-human antibody (gamma or Mu chain specific) diluted 1/1000 in dilution buffer were added to all wells. The plates were then incubated for 1 h at 37° C. Unbound second antibody was removed by washing with PBS, after which 100 μl of the substrate solution were added to all wells. Following incubation for 30 min. at 37° C., the staining reaction was stopped with $H_3PO_4$·HCl solution (50 μl/well) and read at 490 nm. Wells incubated with only dilution buffer instead of CSF were used as background controls.

Results of ELISA Test on Patients' CSF

Cerebrospinal fluid samples from 31 subjects were analyzed by ELISA for the presence of larval antigens and antibodies against larval T. solium antigens. Fifteen of these CSF samples were from control subjects and the remaining 16 were from patients in whom neurocysticercosis was presumed (see Table 2 and "Subjects and Test Samples" above). In 8 of the 16 patients, IHA titers were positive for antibodies in serum and 6 also showed antibodies in CSF with the IHA. Indirect hemagglutination was performed at the CDC in Atlanta and a titer of 1/128 or greater was considered positive (Kagan and Norman, Manual of Clinical Microbiology, American Society for Microbiology, Washington, D.C., 463–466, 1970).

Although all 16 patients were presumed to have neurocysticercosis, the patients were grouped on the basis of confirmation of the presence of larvae by histological procedures (Group I) and the presence or absence (Groups II and III, respectively) of detectable anti-larval antibodies and larval antigens in the CSF.

Eleven CSF samples from the 16 patients exhibited positive ELISA titers when tested for the presence of IgG antibodies against T. solium larvae antigen extract (Groups I and II, Table 3). In comparison, CSF samples from Group III and neurological (Group IV) and normal (Group V) controls showed negative ELISA titers when tested for the presence of IgG antibodies (Table 3). We could not demonstrate the presence of anti-larval IgM antibodies in any of the 31 CSF samples under study (data not shown).

The same group of patients (Groups I and II) in whom CSF samples were positive for antibodies by ELISA, showed positive ELISA titers when tested for the presence of circulating larval antigen in their CSF. These positive titers were obtained at dilutions of CSF as high as 1/320. CSF samples from normal controls and non-cysticercotic patients, as well as Group III, who were diagnosed as having neurocysticercosis, exhibited low ELISA titers (Table 4, Groups III, IV and V). A correlation between ELISA titers and the number of stage of the cysts could not be established since brain CT scans were not available on all patients in Groups I, II and III.

The five patients in Group III, in whom neurocysticercosis was suspected, did not show positive antibody titers by IHA, nor did they show positive titers for antibodies or circulating larval antigen in CSF by ELISA. Two of these five patients (patients No. 12 and 14) came from areas endemic for neurocysticercosis and the evolution and presentation of their clinical signs and symptoms were suggestive of neurocysticercosis. Subsequent to the experiments done in the present study, it was found that patient 13 had a brain metastasis of a lung carcinoma.

The results presented above demonstrate that all patients with histologically confirmed neurocysticercosis (Group I) were identified by ELISA detection of anti-larval IgG antibodies and larval antigens in their CSF. Of the remaining patients (Group II and III) only those in Group II were positive by these assays. Based on the results in the present study, it is predicted that the patients in Group III did not have neurocysticercosis but other neurological disorders. These patients presented signs and symptoms indicative of neurocysticercosis but were negative by IHA and ELISA for anti-larval antibodies and negative also for larval antigens in their CSF using the ELISA described herein.

Each and every publication, patent or otherwise, specifically identified in this specification represents a teaching of the understanding of those skilled in the art at the time this invention was made and is herein individually incorporated by reference to the same extent as if it had been physically reproduced in the location and for the purpose as identified by the context in which it is found.

The invention now being fully described, it will be apparent to one of ordinary skill in the art that many changes and modifications can be made thereto without departing from the spirit or scope of the invention as set forth herein. T,0570 T,0580 T,0590 T,0610

What is claimed as new and desired to be secured by Letters Patent of the United States is:

1. A method for diagnosing active human neurocysticercosis by detecting the presence of at least one *Taenia solium* larval antigen in cererospinal fluid, which comprises:

contacting cerebrospinal fluid from a human to be diagnosed with a solid support, wherein said support binds with a *Taenia solium* larval antigen if present, contacting said support with a first antibody, wherein said first antibody binds with a larval Taenia solium antigen if present in said cerebrospinal fluid, contacting said solid support with a detectable second antibody which will bind with said first antibody, and detecting said second antibody bound to said support.

2. The method of claim 1, wherein said antibody is part of an anti-serum.

3. The method of claim 1, wherein said antiserum is prepared by immunizing an animal with a crude extract of *Taenia solium* larvae.

4. The method of claim 1, wherein said contacting and detecting is carried out on a nitrocellulose disc.

5. The method of claim 1, wherein said detectable second antibody is peroxidase-labeled goat anti-rabbit anti-serum.

6. The method of claim 5, wherein said peroxidase-labeled anti-serum is detected with ophenylene diamine or other peroxidase substrates.

7. A kit for diagnosis of human neurocysticercosis by detecting the presence of at least one *Taenia solium* larval antigen in cerebrospinal fluid, which comprises:

a housing which accomodates a plurality of nitrocellulose or cellulose acetate discs, wherein one disc has coated thereon a *Taenia solium* larval antigen, a first container of a mammalian anti-larval antibody against a *Taenia solium* larval antigen, and a second container of a second antibody reactive with said mammalian anti-larval antibody, said second antibody having conjugated thereto a detectable group.

8. The kit of claim 7, wherein said mammalian anti-larval antibody is rabbit anti-larval anti-serum.

9. The kit of claim 7, wherein said second antibody which is conjugated to a detectable group is peroxidase-labeled goat anti-rabbit anti-serum, and said kit further comprises a third container of a peroxidase substrate.

10. A method for diagnosing active human neurocysticercosis by detecting the presence of at least one *Taenia solium* larval antigen in cerebrospinal fluid, which comprises:

contacting cerbrospinal fluid from a human to be diagnosed with a solid support, wherein said support binds with a single Taenia solium larval antigen if present in cerebrospinal fluid, contacting said support with a first antibody, wherein said first antibody binds with said antigen, and wherein said first antibody is conjugated with at least one biotin molecule, and contacting said support with avidin which is conjugated to a detectable group, and detecting said detectable group bound to said support.

11. The method of claim 10, wherein said detectable group is peroxidase and said detecting is carried out with a peroxidase substrate.

12. The method of claim 11, wherein said substrate is 4-chloro-1-naphthol or other peroxidase substrates.

* * * * *